(12) United States Patent
Ramsey

(10) Patent No.: US 10,022,281 B1
(45) Date of Patent: Jul. 17, 2018

(54) SANITARY PRODUCT DISPOSAL CONTAINERS AND METHODS

(71) Applicant: Shallan Alaura Ramsey, Ashland, OR (US)

(72) Inventor: Shallan Alaura Ramsey, Ashland, OR (US)

(*) Notice: Subject to any disclaimer, the term of this patent is extended or adjusted under 35 U.S.C. 154(b) by 465 days.

(21) Appl. No.: 14/288,458

(22) Filed: May 28, 2014

Related U.S. Application Data (60) Provisional application No. 61/837,680, filed on Jun. 21, 2013.

(51) Int. Cl.
*A61F 13/551* (2006.01)

(52) U.S. Cl.
CPC .................. *A61F 13/5518* (2013.01)

(58) Field of Classification Search
CPC ....... A61F 2013/55155; A61F 13/5518; E01H 2001/126; E01H 2001/1233; E01H 2001/124; E01H 2001/1246
USPC ....... D30/162; 294/1.3; 604/385.13; 141/109
See application file for complete search history.

(56) References Cited

U.S. PATENT DOCUMENTS

| | | | |
|---|---|---|---|
| 2,766,927 A | 10/1956 | Wallace | |
| 3,024,788 A * | 3/1962 | Lane ................... | A61F 13/5518 604/370 |
| 3,193,181 A | 7/1965 | Konjevich et al. | |
| 3,604,423 A * | 9/1971 | Fraser ..................... | A61F 13/56 604/385.13 |
| 3,630,430 A * | 12/1971 | Struble ..................... | B65D 5/18 229/104 |
| 3,865,110 A * | 2/1975 | Traverse ............... | A61F 13/551 604/365 |
| 3,917,333 A * | 11/1975 | Grattan ................. | E01H 1/1206 15/104.8 |
| 3,978,540 A * | 9/1976 | Peck ...................... | E01H 1/1206 294/1.3 |
| 4,551,145 A * | 11/1985 | Ryan .................... | A61F 13/5515 604/385.01 |
| 4,581,027 A * | 4/1986 | Alvarado ............ | A61F 13/5515 604/385.13 |
| 4,741,565 A * | 5/1988 | Bagg ..................... | E01H 1/1206 15/257.1 |

(Continued)

*Primary Examiner* — Paula L Craig
(74) *Attorney, Agent, or Firm* — Jerry Haynes Law

(57) ABSTRACT

Sanitary product disposal containers include an invertible container body having first and second ends, the container body including a first container wall having a first container wall exterior surface; a second container wall carried by the first container wall, the second container wall having a second container wall exterior surface; an end container wall extending between the first container wall and the second container wall generally at the first end of the container body; a concave sanitary product cavity formed by and between the first container wall, the second container wall and the end container wall generally at the first end of the container body; a container opening formed by and between the first container wall and the second container wall generally at the second end of the container body; and a container seal carried by the first container wall exterior surface of the first container wall and the second container wall exterior surface of the second container wall generally at the second end of the container body. Sanitary product disposal methods are also disclosed.

4 Claims, 8 Drawing Sheets

(56) References Cited

U.S. PATENT DOCUMENTS

| | | | | |
|---|---|---|---|---|
| 4,743,240 A * | 5/1988 | Powell | A61F 13/551 | 604/385.13 |
| 4,768,818 A * | 9/1988 | Kolic | A01K 23/005 | 294/1.3 |
| 5,141,505 A * | 8/1992 | Barrett | A61F 13/551 | 604/385.13 |
| 5,149,159 A * | 9/1992 | Bardes | A41D 19/0075 | 294/1.3 |
| 5,222,777 A * | 6/1993 | Clonch | E01H 1/1206 | 294/1.3 |
| 5,358,295 A * | 10/1994 | Campbell | E01H 1/1206 | 294/1.3 |
| 5,564,762 A * | 10/1996 | Ring | E01H 1/1206 | 229/122 |
| 5,579,812 A * | 12/1996 | Bigwood | E01H 1/1206 | 141/108 |
| 5,584,519 A * | 12/1996 | Myles | E01H 1/1206 | 294/1.3 |
| 5,725,268 A * | 3/1998 | Besasie | E01H 1/1206 | 294/1.3 |
| 5,740,554 A * | 4/1998 | Reed | A41D 19/0075 | 2/158 |
| 5,806,668 A * | 9/1998 | Bixby | A41D 19/0068 | 15/227 |
| D418,261 S * | 12/1999 | Betts | D30/162 | |
| 6,059,100 A | 5/2000 | Jones | | |
| 6,225,523 B1 * | 5/2001 | Masini | A61F 13/00038 | 602/58 |
| 6,393,614 B1 * | 5/2002 | Eichelbaum | A41D 19/002 | 2/158 |
| 6,439,627 B1 * | 8/2002 | Devane | E01H 1/1206 | 294/1.3 |
| 6,702,116 B2 | 3/2004 | Hummel | | |
| 6,782,555 B1 * | 8/2004 | Yerelian | A41D 19/0075 | 2/160 |
| 7,278,377 B1 * | 10/2007 | Stephens | E01H 1/1206 | 119/867 |
| 8,282,280 B2 | 10/2012 | Germanow et al. | | |
| 2001/0049838 A1 * | 12/2001 | Fitz | A41D 19/0075 | 2/21 |
| 2002/0178482 A1 * | 12/2002 | Samuelsson | A61F 13/551 | 2/16 |
| 2003/0222465 A1 * | 12/2003 | Fonfrias | E01H 1/1206 | 294/1.3 |
| 2004/0098794 A1 * | 5/2004 | Ernest | A47K 11/12 | 4/144.2 |
| 2004/0103467 A1 * | 6/2004 | Schmitt | A47K 7/02 | 2/159 |
| 2004/0188443 A1 * | 9/2004 | Perkitny | E01H 1/1206 | 220/495.06 |
| 2004/0221367 A1 * | 11/2004 | Darrow | A41D 19/0075 | 2/167 |
| 2005/0098466 A1 | 5/2005 | Thomas | | |
| 2005/0182375 A1 * | 8/2005 | Kropf | A61F 13/5512 | 604/385.01 |
| 2005/0182379 A1 * | 8/2005 | Olsen | A61F 13/551 | 604/385.13 |
| 2005/0264016 A1 * | 12/2005 | Davis | E01H 1/1206 | 294/1.3 |
| 2006/0045391 A1 | 3/2006 | Reglar | | |
| 2006/0204558 A1 * | 9/2006 | Kantner | A01N 25/34 | 424/443 |
| 2006/0279097 A1 * | 12/2006 | Jones | E01H 1/1206 | 294/1.3 |
| 2007/0055213 A1 | 3/2007 | Erekson | | |
| 2007/0239127 A1 | 10/2007 | Bridges | | |
| 2008/0101731 A1 * | 5/2008 | Carlson | E01H 1/1206 | 383/41 |
| 2009/0072558 A1 * | 3/2009 | Hanson | E01H 1/1206 | 294/1.3 |
| 2009/0112148 A1 * | 4/2009 | Morrow | A61F 13/26 | 604/14 |
| 2009/0282786 A1 * | 11/2009 | Bland | B65B 67/00 | 53/469 |
| 2009/0315349 A1 * | 12/2009 | Black | E01H 1/1206 | 294/1.3 |
| 2011/0106034 A1 * | 5/2011 | Kramer | A61F 13/551 | 604/359 |
| 2011/0210571 A1 * | 9/2011 | Dan | A41D 19/0024 | 294/1.3 |
| 2012/0035577 A1 * | 2/2012 | Tomes Dietz | A61F 13/15 | 604/385.24 |
| 2012/0226256 A1 * | 9/2012 | Ung | A61F 13/5515 | 604/385.13 |
| 2014/0265381 A1 * | 9/2014 | Joseph-de Saram | E01H 1/1206 | 294/1.3 |

\* cited by examiner

SANITARY PRODUCT DISPOSAL CONTAINERS AND METHODS

CROSS-REFERENCE TO RELATED APPLICATIONS

This application claims the benefit of U.S. provisional application No. 61/837,680, filed Jun. 21, 2013 and entitled MASK IT, which provisional application is incorporated by reference herein in its entirety.

FIELD OF THE INVENTION

The background description provided herein is solely for the purpose of generally presenting the context of the illustrative embodiments of the disclosure. Aspects of the background description are neither expressly nor impliedly admitted as prior art against the claimed subject matter.

Illustrative embodiments of the disclosure generally relate to sanitary products such as feminine hygiene products. More particularly, illustrative embodiments of the disclosure relate to sanitary product disposal containers and methods which can be used to discreetly dispose of a sanitary product while eliminating leakage of fluids and odors without a user's having to touch or handle the product.

BACKGROUND OF THE INVENTION

Sanitary product disposal devices are well known in the art. Conventional sanitary product disposal devices may, however, not be effective in blocking odors and may not prevent the leaking of fluids. Moreover, conventional products may be cumbersome, inconvenient or indiscreet to use and may require that the user touch or handle the used product prior to disposal. Additionally, conventional products may involve complicated, expensive and overly-difficult assembly and/or disassembly of parts.

Currently, there does not exist a suitable manner to dispose of used feminine sanitary products. Conventional sanitary products must be disposed in the trash as they are not suitable for being flushed down the toilet. Thus, the used products may emit a disagreeable odor and may attract children and pets.

Accordingly, sanitary product disposal containers and methods which can be used to discreetly dispose of a sanitary product while eliminating leakage of fluids and odors without a user's having to touch or handle the product are needed.

SUMMARY OF THE INVENTION

Illustrative embodiments of the disclosure are generally directed to sanitary product disposal containers which can be used to discreetly dispose of a sanitary product while eliminating leakage of fluids and odors without a user's having to touch or handle the product. An illustrative embodiment of the sanitary product disposal container includes an invertible container body having first and second ends, the container body including a first container wall having a first container wall exterior surface; a second container wall carried by the first container wall, the second container wall having a second container wall exterior surface; an end container wall extending between the first container wall and the second container wall generally at the first end of the container body; a concave sanitary product cavity formed by and between the first container wall, the second container wall and the end container wall generally at the first end of the container body; a container opening formed by and between the first container wall and the second container wall generally at the second end of the container body; and a container seal carried by the first container wall exterior surface of the first container wall and the second container wall exterior surface of the second container wall generally at the second end of the container body.

Illustrative embodiments of the disclosure are further generally directed to sanitary product disposal methods. An illustrative embodiment of the sanitary product disposal method includes providing a sanitary product disposal container, inserting fingers of a hand into the sanitary product disposal container, grasping a sanitary product with the fingers through a container wall of the sanitary product disposal container, internalizing the sanitary product into the sanitary product disposal container by inverting the sanitary product disposal container and sealing the sanitary product disposal container.

BRIEF DESCRIPTION OF THE DRAWINGS

Illustrative embodiments of the disclosure will now be described, by way of example, with reference to the accompanying drawings, in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is non-limiting and is not necessarily to be construed as preferred or advantageous over other implementations. All of the implementations described below are exemplary implementations provided to enable persons skilled in the art to practice the disclosure and are not intended to limit the scope of the appended claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description. Relative terms such as "upper", "lower", "front", 'rear", "side", "interior" and "exterior" as used herein are intended for descriptive purposes only and are not necessarily intended to be construed in a limiting sense.

Figure 1:
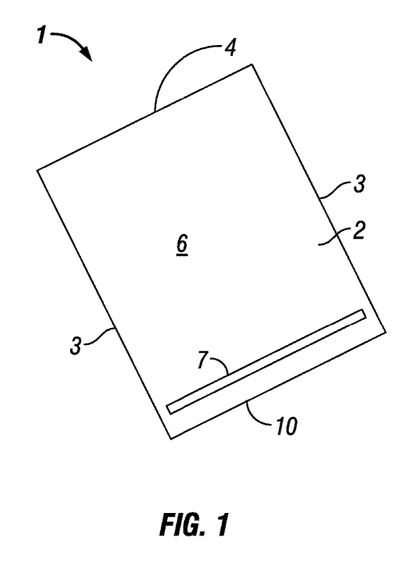
FIG. 1 is a front perspective view of an illustrative embodiment of the sanitary product disposal containers in an open position.
Figure 2:
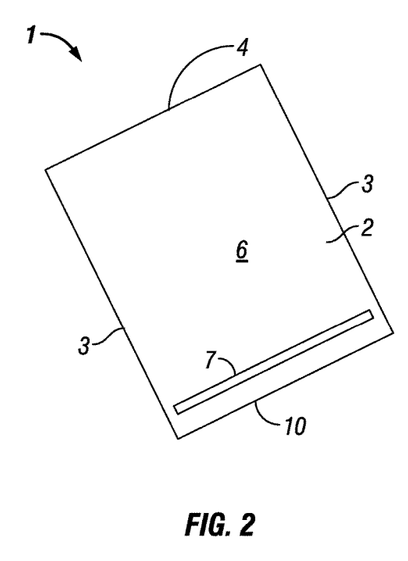
FIG. 2 is a front perspective view of an illustrative embodiment of the sanitary product disposal containers in a closed position.
Figure 3:
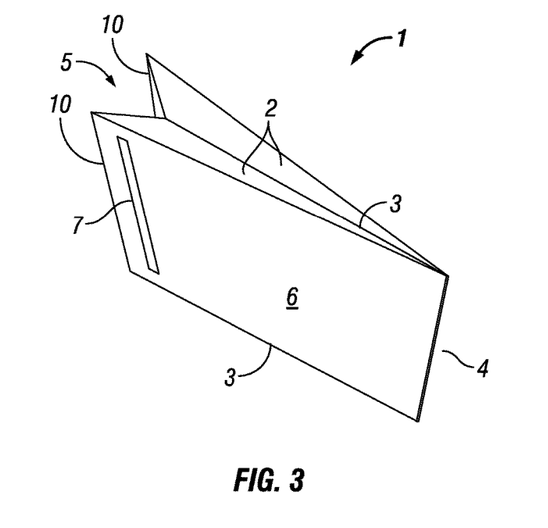
FIG. 3 is a rear perspective view of an illustrative embodiment of the sanitary product disposal containers in an open position.
Figure 6:
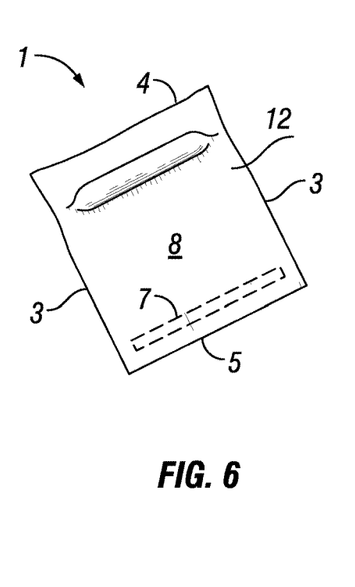
FIG. 6 is a perspective view of the illustrative sanitary product disposal container with the sanitary product internalized in the container and the container sealed.
Figure 7:
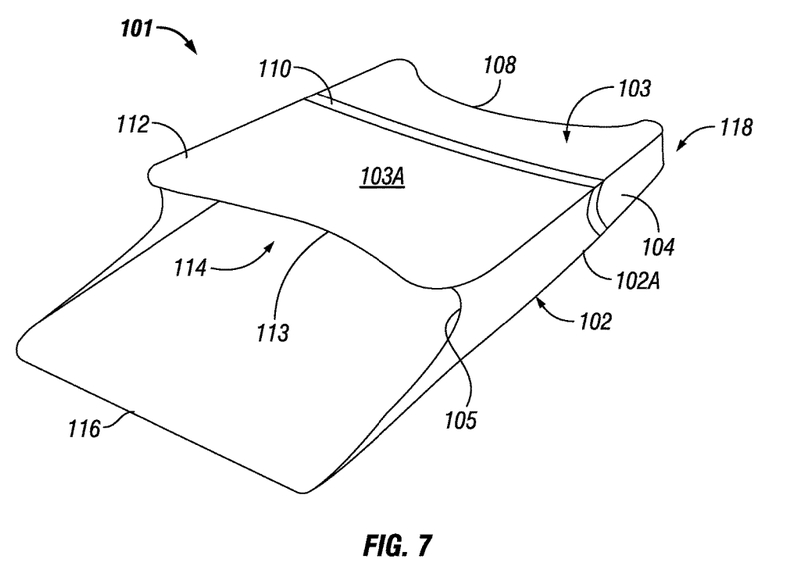
FIG. 7 is a front perspective view of an alternative illustrative embodiment of the sanitary product disposal container.

Referring initially to FIGS. 1-6 of the drawings, an illustrative embodiment of a sanitary product disposal container, hereinafter container, is generally indicated by reference numeral 1. As illustrated in FIGS. 1-3, the container 1 may include a pair of container walls 2 which may be generally rectangular. The container walls 2 may be joined along a pair of side container edges 3 and a front container edge 4. A container opening 5 may be formed between the container walls 2 at a rear container edge 10. Each of the container walls 2 may have an exterior wall surface 6 and an interior wall surface 8 (FIG. 6).

A pair of container seals 7 may be provided on the exterior wall surfaces 6 of the respective container walls 2 generally at or adjacent to the rear container edge 10. The container seals 7 may be any type of seals which are known by those skilled in the art and suitable for sealing the container opening 5 with a liquid-tight and airtight seal. For example and without limitation, in some embodiments, the container seals 7 may include a reversible compartment seal such as a ZIP-LOCK® seal which is widely used for sealing sandwich bags and the like. In other embodiments, the container seals 7 may include an adhesive.

The container 1 may be fabricated as a small bag made of an opaque, liquid-impermeable material which blocks the release or emission of smells and fluids. In some embodiments, the container 1 may be fabricated of a biodegradable plastic with elasticity similar to that of a rubber glove. The container 1 may be fabricated in different sizes with various dimensions depending on functional requirements.

Figure 4:
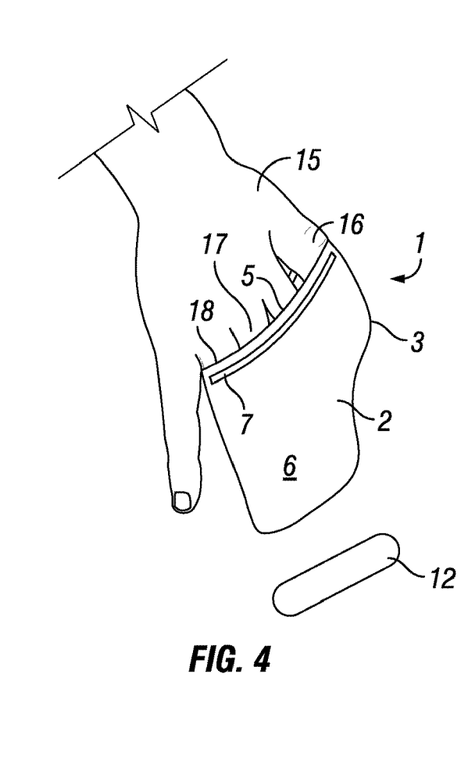
FIG. 4 is a perspective view of an illustrative sanitary product disposal container with a user's thumb, index finger and middle finger extending into the container preparatory to internalizing a sanitary product in the container in exemplary application of the container.
Figure 5:
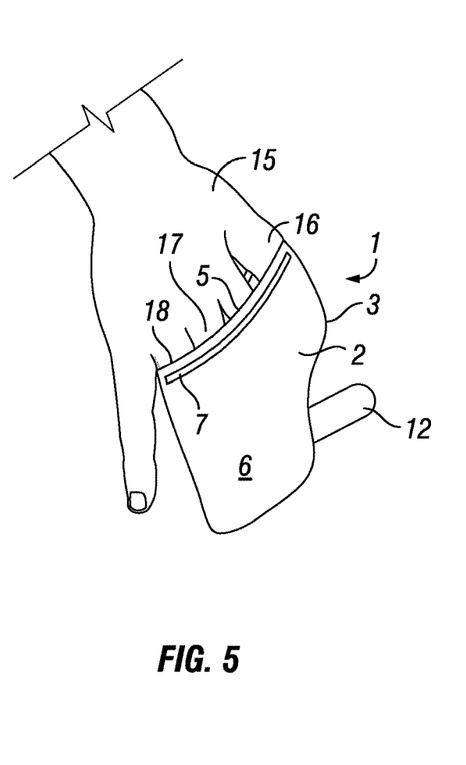
FIG. 5 is a perspective view of the illustrative sanitary product disposal container illustrated in FIG. 4, with the user grasping the sanitary product.

As illustrated in FIGS. 4-6, in exemplary application, the container 1 is used to dispose of a used sanitary product 12. Accordingly, as illustrated in FIG. 4, with the exterior wall surfaces 6 of the container walls 2 facing outwardly, a user inserts her thumb 16, index finger 17 and middle finger 18 into the container opening 5 (FIG. 3) of the container 1 such that the container 1 is worn on the user's hand 15 like a glove. The user then grasps the sanitary product 12 with the fingers through the container walls 2. Next, the user inverts, or turns the container 1 inside out, such that the exterior wall surfaces 6 now face the interior of the container and the interior wall surfaces 8 face exteriorly, as illustrated in FIG. 6. The container seals 7 on the respective container walls 2 are pressed together to seal the interior from the exterior of the container 1, and liquids and odors are sealed in the container 1. Finally, the container 1 with the used sanitary product 12 contained therein may be discarded.

It will be appreciated by those skilled in the art that the sanitary product disposal container 1 provides an inconspicuous and sanitary method for disposing of used feminine sanitary products 12. The sanitary product disposal container 1 can be packaged in a variety of ways depending on the application. For example and without limitation, for home use, multiple sanitary product disposal containers 1 may be packaged in decorative boxes. For public restroom use, multiple sanitary product disposal containers 1 may be packaged in a wall-mounted dispenser for convenience of use. Moreover, the sanitary product disposal container 1 may eliminate the need to use toilet paper to wrap and conceal the used sanitary product 12 for disposal in a trash receptacle and reduces the likelihood that the used sanitary product 12 will be flushed down the toilet.

Figure 8:
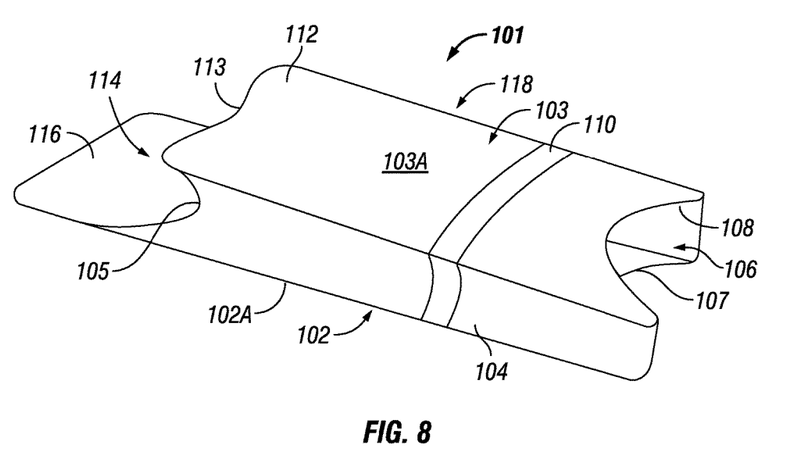
FIG. 8 is a right side perspective view of the illustrative sanitary product disposal container illustrated in FIG. 7.
Figure 9:
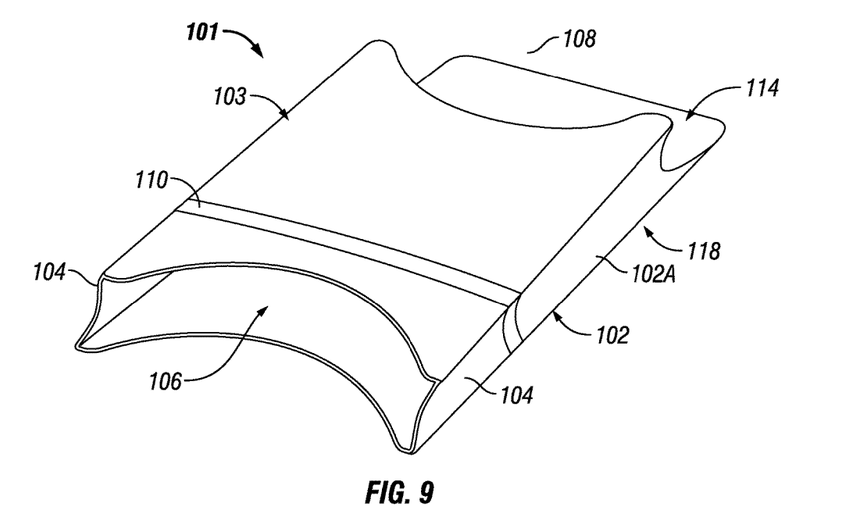
FIG. 9 is a rear perspective view of the illustrative sanitary product disposal container illustrated in FIG. 7.
Figure 10:
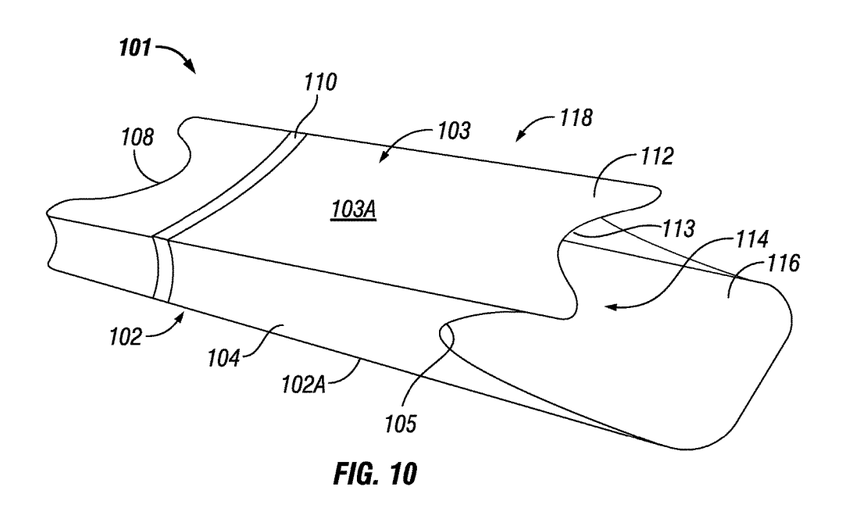
FIG. 10 is a left side perspective view of the illustrative sanitary product disposal container illustrated in FIG. 7.
Figure 11:
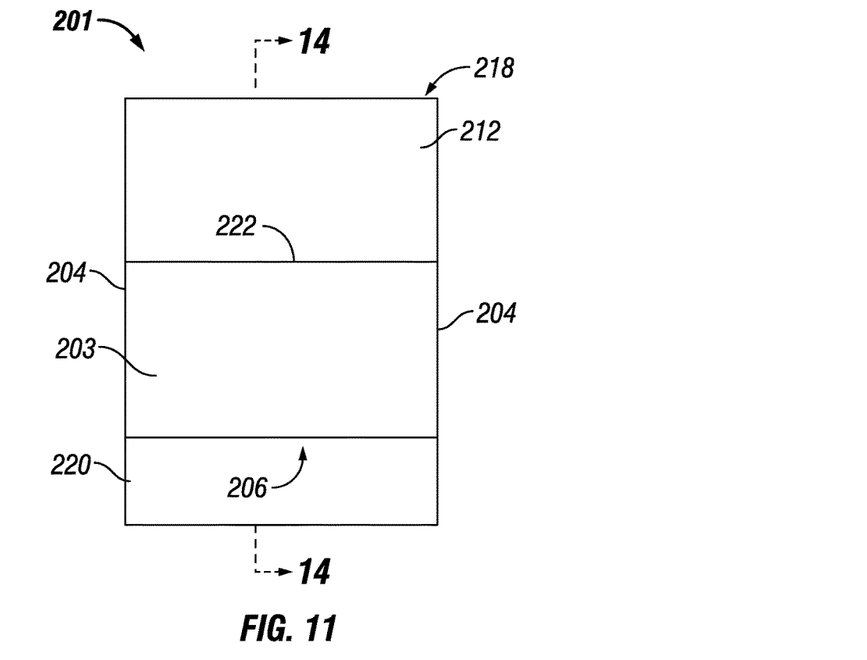
FIG. 11 is a top view of another alternative illustrative embodiment of the sanitary product disposal container.
Figure 12:
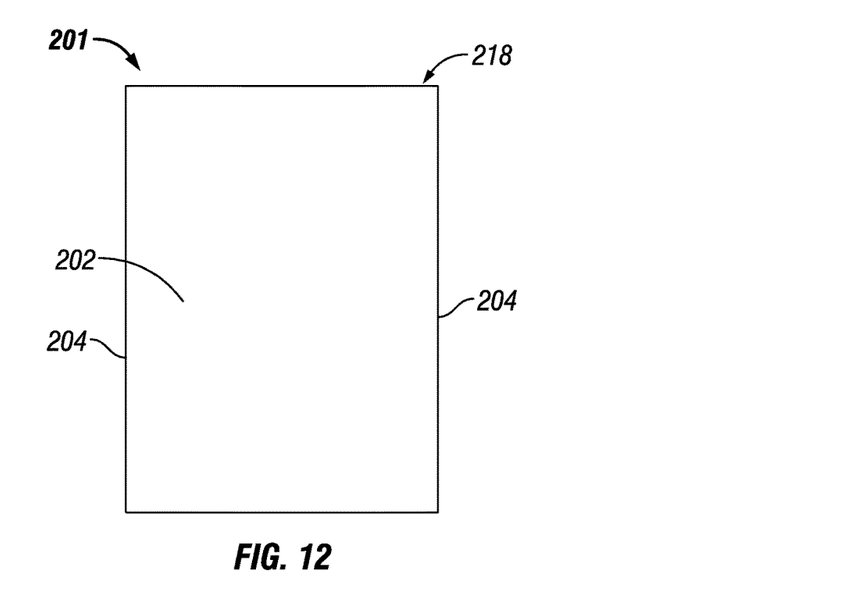
FIG. 12 is a bottom view of the illustrative sanitary product disposal container illustrated in FIG. 11.
Figure 13:
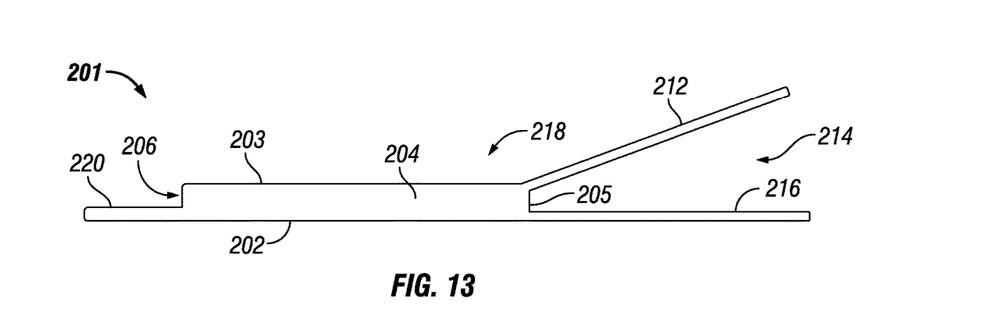
FIG. 13 is a side view of the illustrative sanitary product disposal container illustrated in FIG. 11.
Figure 14:
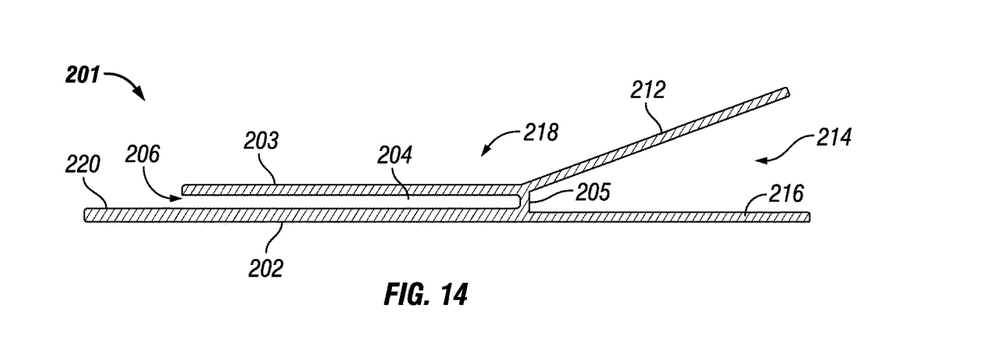
FIG. 14 is a longitudinal sectional view, taken along section lines 14-14 in FIG. 11.

Referring next to FIGS. 7-10 of the drawings, an alternative illustrative embodiment of the sanitary product disposal container, hereinafter container, is generally indicated by reference numeral 101. Unless otherwise noted, the container 101 may be fabricated of the same materials of construction as the container 1 which was heretofore described with respect to FIGS. 1-3. The container 101 may include a generally elongated container body 118 having a lower container wall 102 and an upper container wall 103. The lower container wall 102 may have a lower container wall exterior surface 102a. The upper container wall 103 may have an upper container wall exterior surface 103a. A pair of side container walls 104 may extend between the lower container wall 102 and the upper container wall 103. An end container wall 105 may extend between the lower container wall 102 and the upper container wall 103 at generally a front end of the container body 118. A container opening 106 may be formed by and between the lower container wall 102, the upper container wall 103 and the side container walls 104 at generally a rear end of the container body 118. As illustrated in FIG. 8, a lower wall indentation 107 and an upper wall indentation 108 may be provided in the lower container wall 102 and the upper container wall 103, respectively, at the container opening 106. Container seals 110 may be provided on the lower container wall exterior surface 102a of the lower container wall 102 and the upper container wall exterior surface 103a of the upper container wall 103, generally at or adjacent to the container opening 106.

A lower wall gusset 116 may extend from the lower container wall 102 beyond the end container wall 105. An upper wall gusset 112 may extend from the upper container wall 103 beyond the end container wall 105 and in spaced-apart relationship to the lower wall gusset 116. In some embodiments, a gusset indentation 113 may be provided in the upper wall gusset 112 for purposes which will be hereinafter described. A concave sanitary product cavity 114 may be formed by and between the end container wall 105, the upper wall gusset 112 and the lower wall gusset 116. The container 101 may be fabricated in different sizes with various dimensions depending on functional requirements.

In exemplary application, the container 101 may be used to dispose of a used sanitary product (not illustrated). Accordingly, the hand of a user is inserted into the container 101 through the container opening 106 such that the container 101 is worn on the user's hand like a glove. The user then maneuvers the container 101 until the sanitary product is cradled in the sanitary product cavity 114 between the upper wall gusset 112 and the lower wall gusset 116, after which the user grasps the sanitary product with the fingers through the end container wall 105. The lower wall indentation 107 and the upper wall indentation 108 may create an easy-open tab for the container opening 106. Next, the user inverts, or turns the container 101 inside out, such that the exterior wall surfaces of the lower container wall 102, the upper container wall 103 and the side container walls 104 now face the interior of the container 101 and the interior wall surfaces face exteriorly. The user may grasp the gusset indentation 113 with the thumb of the opposite hand to facilitate inversion of the container 101. The container seals 110 on the respective lower container wall 102 and upper container wall 103 are pressed together to seal the interior from the exterior of the container 101, and liquids and odors are sealed in the container 101. Finally, the container 101 with the used sanitary product contained therein is discarded.

Referring next to FIGS. 11-14 of the drawings, another alternative illustrative embodiment sanitary product disposal container, hereinafter container, is generally indicated by reference numeral 201. In the container 201, elements which are analogous to the respective elements of the container 101 that was heretofore described with respect to FIGS. 7-10 are designated by the same numeral in the 201-299 series in FIGS. 11-14. A wall overhang 220 may extend from the lower container wall 202 beyond the container opening 206. Application of the container 201 may be as was heretofore described with respect to the container 101 in FIGS. 7-10. The container 201 may be fabricated in different sizes with various dimensions depending on functional requirements.

Figure 15:
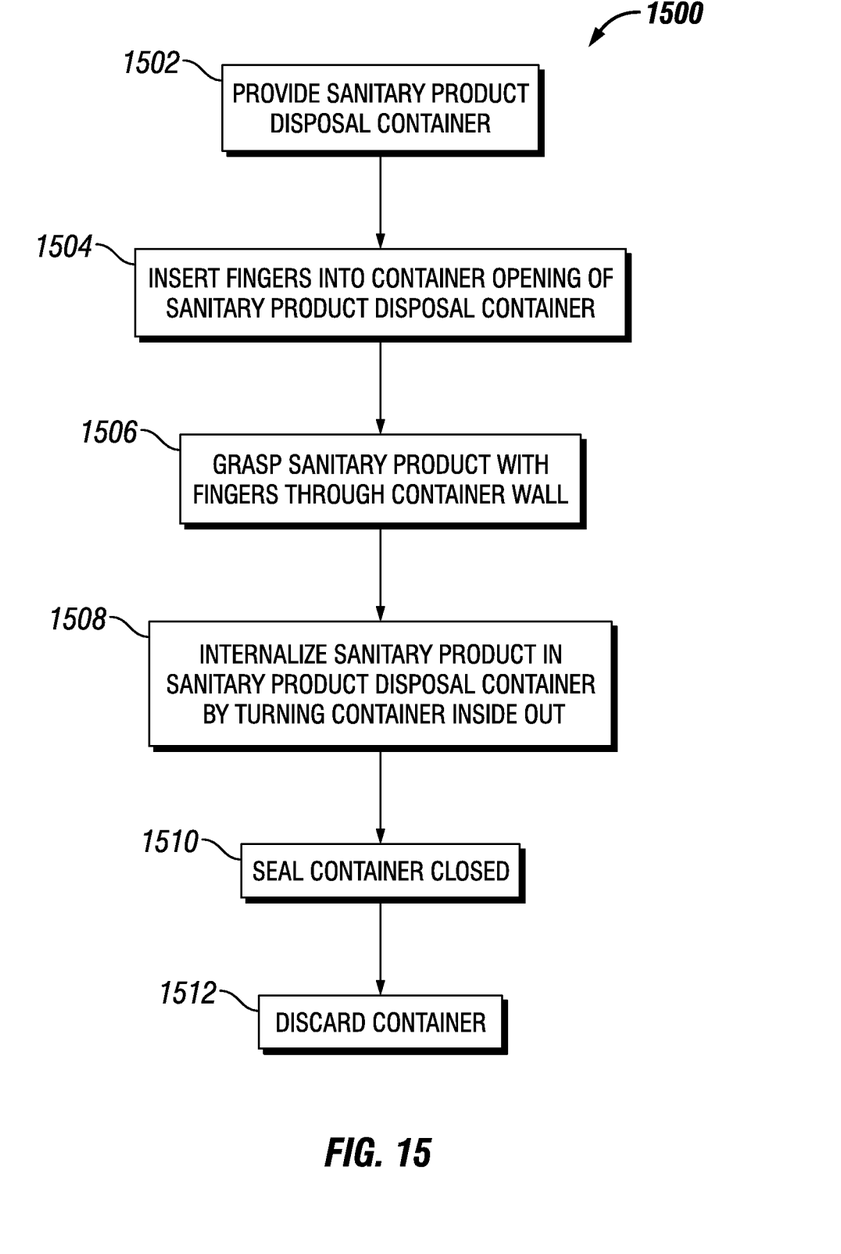
FIG. 15 is a flow diagram of an illustrative embodiment of a sanitary product disposal method.

Referring next to FIG. 15 of the drawings, a flow diagram 1500 of an illustrative embodiment of a sanitary product disposal method is shown. At block 1502, a sanitary product disposal container is provided. In some embodiments, the sanitary product disposal container may have a design which is the same as or similar to the sanitary product disposal container 1 which was heretofore described with respect to FIGS. 1-6. At block 1504, fingers on the hand of a user are inserted into a container opening of the container. At block 1506, the user grasps the sanitary product through the container wall of the container. At block 1508, the sanitary product is internalized into the container by turning the container inside out. At block 1510, the container is sealed closed. In some embodiments, the container may be sealed closed using a reversible compartment seal. In some embodiments, the container may be sealed closed using an adhesive. At block 1512, the container may be discarded.

Figure 16:
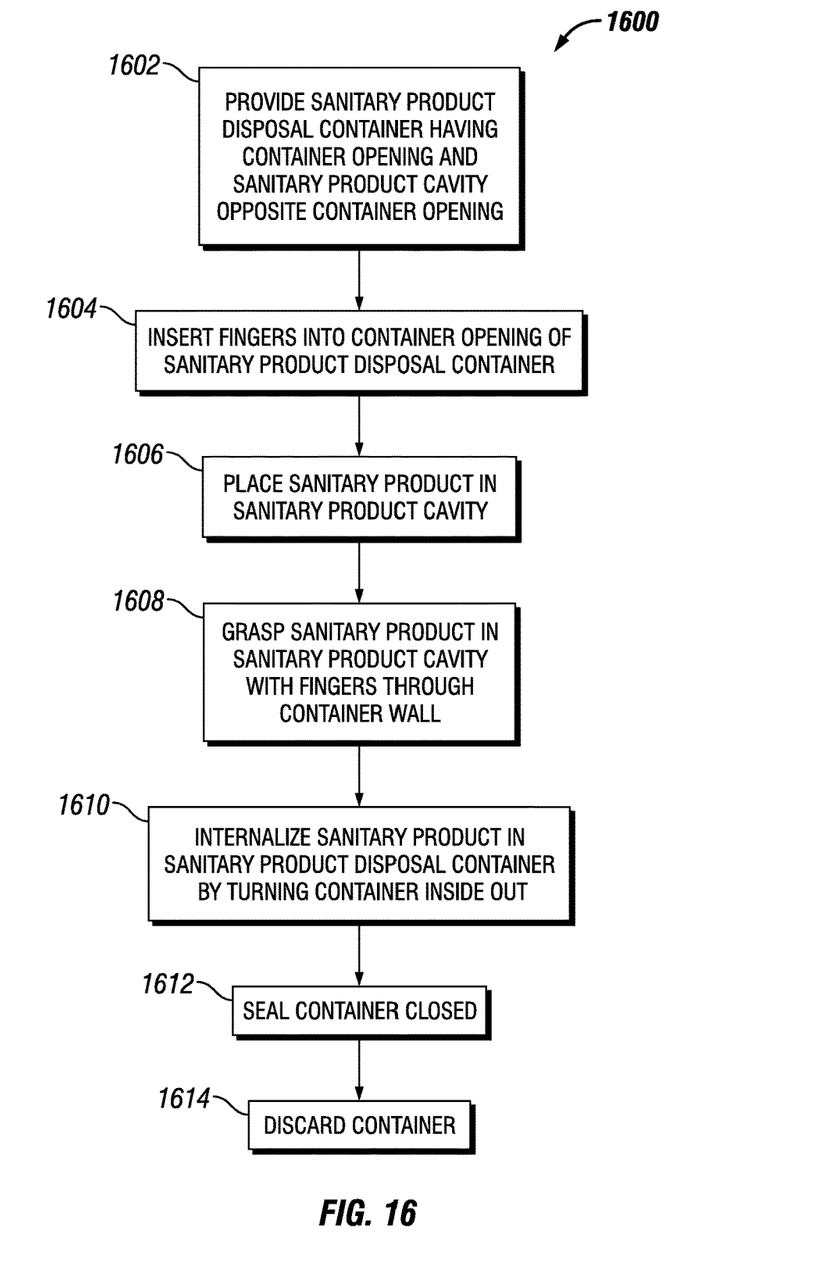
FIG. 16 is a flow diagram of another illustrative embodiment of a sanitary product disposal method.

Referring next to FIG. 16 of the drawings, a flow diagram 1600 of another illustrative embodiment of a sanitary product disposal method is shown. At block 1602, a sanitary product disposal container is provided. In some embodiments, the sanitary product disposal container may have a design which is the same as or similar to the sanitary product disposal container 101 which was heretofore described with respect to FIGS. 7-10. In some embodiments, the sanitary product disposal container may have a design which is the same as or similar to the sanitary product disposal container 201 which was heretofore described with respect to FIGS. 11-14. The sanitary product disposal container includes a container opening and a sanitary product cavity opposite the container opening. At block 1604, fingers on the hand of a user are inserted into a container opening of the container. At block 1606, the user maneuvers the container such that the sanitary product is cradled in the sanitary product cavity of the container. At block 1608, the user grasps the sanitary product with the fingers through the container wall of the container. At block 1610, the sanitary product is internalized into the container by turning the container inside out. At block 1612, the container is sealed closed. At block 1614, the container may be discarded.

While illustrative embodiments of the disclosure have been described above, it will be recognized and understood that various modifications can be made in the disclosure and the appended claims are intended to cover all such modifications which may fall within the spirit and scope of the disclosure.

What is claimed is:
1. A sanitary product disposal container, comprising:
an invertible container body having first and second ends, the container body including:
a first container wall having a first container wall exterior surface in a non-inverted configuration of the container body;
a second container wall attached to the first container wall, the second container wall having a second container wall exterior surface, the container body invertible such that the container body is turned outside in in an inverted configuration of the container body, with the first container wall exterior surface and the second container wall exterior surface facing an interior of the container body in the inverted configuration of the container body;
a pair of side container walls extending between the first container wall and the second container wall;
an end container wall extending between the first container wall and the second container wall generally at the first end of the container body;
a concave sanitary product cavity formed by and between the first container wall, the second container wall and the end container wall generally at the first end of the container body;
a first wall gusset extending from the first container wall beyond the sanitary product cavity;
a second wall gusset extending from the second container wall beyond the sanitary product cavity, the first wall gusset extends beyond the second wall gusset;
an exterior concave gusset indentation in the second wall gusset, the gusset indentation extending between the pair of side container walls;
a container opening formed by and between the first container wall and the second container wall generally at the second end of the container body; and
a container seal attached to the first container wall exterior surface of the first container wall and the second container wall exterior surface of the second container wall generally at the second end of the container body, the container seal disposed inside the container body and securable in the inverted configuration of the container body when the container body is turned outside in.

2. The sanitary product disposal container of claim 1 wherein the container seal comprises a reversible compartment seal.

3. The sanitary product disposal container of claim 1 wherein the container seal comprises an adhesive.

4. The sanitary product disposal container of claim 1 further comprising a first wall indentation in the first container wall and a second wall indentation in the second container wall at the container opening.

\* \* \* \* \*